United States Patent
Nousiainen (10) Patent No.: US 10,349,889 B2
(45) Date of Patent: Jul. 16, 2019

(54) PORTABLE BIOMETRIC WRIST DEVICE AND A METHOD FOR MANUFACTURING THEREOF

(71) Applicant: PulseOn Oy, Espoo (FI)

(72) Inventor: Jari Nousiainen, Espoo (FI)

(73) Assignee: PULSEON OY, Espoo (FI)

(*) Notice: Subject to any disclaimer, the term of this patent is extended or adjusted under 35 U.S.C. 154(b) by 0 days.

(21) Appl. No.: 15/514,331

(22) PCT Filed: Sep. 30, 2015

(86) PCT No.: PCT/FI2015/050646
§ 371 (c)(1),
(2) Date: Mar. 24, 2017

(87) PCT Pub. No.: WO2016/051016
PCT Pub. Date: Apr. 7, 2016

(65) Prior Publication Data
US 2017/0281081 A1  Oct. 5, 2017

(30) Foreign Application Priority Data
Oct. 3, 2014  (FI) .................................... 20145862

(51) Int. Cl.
*A61B 5/024* (2006.01)
*A61B 5/00* (2006.01)

(52) U.S. Cl.
CPC .......... *A61B 5/681* (2013.01); *A61B 5/02427* (2013.01); *A61B 5/02438* (2013.01);
(Continued)

(58) Field of Classification Search
CPC ............ A61B 5/02427; A61B 5/02438; A61B 5/02444; A61B 5/7257; A61B 5/681; A61B 2562/185; A61B 2562/12; A61B 5/02433
See application file for complete search history.

(56) References Cited

U.S. PATENT DOCUMENTS 6,119,031 A * 9/2000 Crowley .............. A61B 5/0075
                                                         600/310
7,139,076 B1  11/2006 Marbach
(Continued)

FOREIGN PATENT DOCUMENTS

CN          1629753 A     6/2005
CN       102727220 A    10/2012
(Continued)

OTHER PUBLICATIONS

International Search Report, Application No. PCT/FI2015/050646, dated Dec. 15, 2015, 4 pages.
(Continued)

*Primary Examiner* — Elmer M Chao
(74) *Attorney, Agent, or Firm* — Ziegler IP Law Group, LLC (57) ABSTRACT

A portable biometric wrist device having an optical sensor and including at least one light source and at least one light detector installed onto a circuit board, a casing having at least one aperture for said at least one light source and at least one aperture for said at least one light detector, wherein each of said at least one light source and at least one light detector are optically isolated from each other inside said casing with a sealing plate between said casing and said circuit board, said sealing plate having at least one aperture for said at least one light source and at least one aperture for said at least one light detector. The present invention also provides a method for manufacturing said portable biometric wrist device.

35 Claims, 8 Drawing Sheets

(52) U.S. Cl.
CPC ....... *A61B 5/02444* (2013.01); *A61B 2562/12* (2013.01); *A61B 2562/185* (2013.01)

(56) References Cited

U.S. PATENT DOCUMENTS

| | | | | |
|---|---|---|---|---|
| 7,479,108 | B2* | 1/2009 | Rini | ................. A61B 5/0031 600/300 |
| 8,216,078 | B1* | 7/2012 | Yovanovich | ......... A63D 15/005 473/1 |
| 8,460,197 | B1 | 6/2013 | Brady et al. | |
| 8,611,976 | B2* | 12/2013 | Gonopolskiy | ....... A61B 5/0059 600/310 |
| 2003/0181794 | A1 | 9/2003 | Rini et al. | |
| 2007/0244398 | A1 | 10/2007 | Lo et al. | |
| 2008/0097221 | A1* | 4/2008 | Florian | .............. A61B 5/02433 600/476 |
| 2010/0317937 | A1 | 12/2010 | Kuhn et al. | |
| 2012/0197093 | A1 | 8/2012 | LeBoeuf et al. | |
| 2013/0137994 | A1 | 5/2013 | Sawada et al. | |
| 2014/0221854 | A1 | 8/2014 | Wai | |
| 2014/0275891 | A1 | 9/2014 | Muehlemann et al. | |
| 2014/0288435 | A1 | 10/2014 | Richards et al. | |
| 2014/0371601 | A1 | 12/2014 | Fei | |
| 2015/0346766 | A1* | 12/2015 | Justice | ................... G06F 1/163 361/679.03 |

FOREIGN PATENT DOCUMENTS

| | | |
|---|---|---|
| CN | 103092055 A | 5/2013 |
| CN | 103919536 A | 7/2014 |
| EP | 2745771 A1 | 6/2014 |
| WO | 2005004711 A1 | 1/2005 |
| WO | 2013027359 A1 | 2/2013 |

OTHER PUBLICATIONS

International Preliminary Report on Patentability, Application No. PCT/FI2015/050646, dated Dec. 30, 2016, 24 pages.
Finnish Patent and Registration Office, Office Action, Application No. 20145862, dated Jun. 3, 2015, 7 pages.
Written Opinion of the International Searching Authority, Application No. PCT/FI2015/050646, dated Dec. 21, 2015, 7 pages.
Written Opinion of the International Preliminary Examining Authority, Application No. PCT/FI2015/050646, dated Sep. 2, 2016, 8 pages.
Finnish Patent and Registration Office, Office Action, Application No. 20145862, dated Sep. 19, 2016, 8 pages.
Extended European Search Report, Application No. 15847611.9, dated Apr. 18, 2018, 7 pages.
National Intellectual Property Administration, P.R. China, First Office Action, dated Feb. 2, 2019, Patent Application 2015800540002.1, Application Date Sep. 30, 2015. (25 Pages).

* cited by examiner

PORTABLE BIOMETRIC WRIST DEVICE AND A METHOD FOR MANUFACTURING THEREOF

FIELD OF THE APPLICATION

The present application relates to a portable biometric wrist device having an optical sensor, and to a method for manufacturing said device. More particularly the present application relates to a portable biometric wrist device having an optical sensor wherein a light detector and a light source are optically isolated from each other.

BACKGROUND

Physiological data can be measured from a user by using portable biometric monitors, which may be attached to the user, for example to the chest, wrist, forearm, or arm of the user. The physiological data may include for example heart rate. Traditional monitors usually contain a separate sensor, which is attached for example to the user's chest with a strap, and which communicates wirelessly with a wrist device. The use of separate sensors complicates the use of a portable biometric monitor, and therefore there is a need to develop solutions embedded to the wrist-attached or other extremity attached device.

One way for measuring the heart rate is using optical measurement. The optical heart rate measurement is based on the fact that light is emitted by a light source towards body tissue and at least one detector is configured to detect the intensity of reflected light after propagation through the body tissue.

In such measurement a photoplethysmogram (PPG) is obtained. It is an optically obtained plethysmogram, a volumetric measurement of an organ. A PPG is often obtained by using a pulse oximeter which illuminates the skin and measures changes in light absorption. With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak.

The change in volume caused by the pressure pulse may be detected for example by illuminating the skin with the light from a light-emitting diode (LED) and then measuring the amount of light either transmitted or reflected to a photodiode. Each cardiac cycle appears as a downward peak in the photodiode. Because blood flow to the skin can be modulated by multiple other physiological systems, the PPG can also be used to monitor breathing, hypovolemia, and other circulatory conditions. Additionally, the shape of the PPG waveform differs from subject to subject, and varies with the location and manner in which the pulse oximeter is attached.

The implementation of the optical sensors as well as manufacturing thereof needs further improvement to obtain sensors which are more sensitive and accurate, and which are mechanically durable. If an optical sensor is provided as a module, it may have optical leakage wherein light leaks from the light source to the light detector already in the module causing problems in the measurement.

Especially the manufacture of wrist devices is challenging. Such devices are relatively small and usually contain the required electronics, display, optical components and other parts of the device all packed in a flat closed casing. Therefore the assembly of the parts requires extreme accuracy.

SUMMARY

One embodiment provides a portable biometric wrist device having an optical sensor and comprising
at least one light source and at least one light detector installed onto a circuit board,
a casing having at least one aperture for said at least one light source and at least one aperture for said at least one detector, wherein
each of said at least one light source and at least one light detector are optically isolated from each other inside said casing with a sealing plate between said casing and said circuit board, said sealing plate having at least one aperture for said at least one light source and at least one aperture for at said least one light detector.

One embodiment provides a method for manufacturing a portable biometric wrist device having an optical sensor, the method comprising
providing
  at least one light source and at least one light detector installed onto a circuit board,
  a casing having at least one aperture for said at least one light source and at least one aperture for said at least one light detector, and
  a sealing plate arranged to fit between said casing and said circuit board, said sealing plate having at least one aperture for said at least one light source and at least one aperture for at said least one light detector, and
combining said circuit board, said sealing plate and said casing so that said at least one light source and said at least one light detector fit to the apertures in the sealing plate for optically isolating said at least one light source and at least one light detector from each other inside said casing.

The main embodiments are characterized in the independent claims. Various embodiments are disclosed in the dependent claims. The features recited in dependent claims and in the specification are mutually freely combinable unless otherwise explicitly stated.

The feature that the at least one light detector and the at least one light source are optically isolated from each other inside the casing provides an effect of preventing leakage of light inside the device between the light source and the light detector. The light detected by the light detector comes only from outside the device. This enhances the sensitivity and the accuracy of the measurement providing better signal to noise ratio and signal to DC values.

Providing a separate pre-fabricated and pre-fitted sealing plate facilitates the manufacture of the wrist device. For example when compared to solutions wherein an optical sensor is molded into resin, in the present embodiments there is no need to prepare and apply resin or wait for the resin to cure. The use of a ready-made sealing plate also enables the high accuracy of the manufacture as the size and the form of the plate and the apertures are always correct and fit to the other parts without any further working phases or fitting. This renders the manufacturing process simple and fast thus saving time and money. The error percentage is also very low when a pre-fabricated sealing plate is used. There is no need to use specific equipment and/or to apply adhesives or resins during the assembly of the light isolating parts.

The elastic sealing plate also acts as an intermediate layer between the circuit board and the bottom of the casing. Any roughness or protruding parts in the circuit board or in the inner side of the casing will be buried in the elastic material, which makes the construction waterproof and provides shock-absorbing properties.

Non-waterproof compounds and solutions may be used in the constructions according to embodiments. Such optical components may be used which do not tolerate external stress, such as moisture, dirt or mechanical stress. This is not possible for example if the parts are molded into resin and exposed from the molded part.

BRIEF DESCRIPTION OF THE FIGURES

FIGS. 1A and 1B show two different orientations of the pivots and demonstrate the pivoted movement of the device.

FIG. 3A shows inner parts of a device related to the grounding, wherein

DETAILED DESCRIPTION

One embodiment provides a portable biometric device having an optical sensor comprising at least one light source and at least one light detector installed on a circuit board, a casing having at least one aperture for said at least one light source and at least one aperture for said at least one light detector, and a sealing plate between said casing and said circuit board, said sealing plate having at least one aperture for said at least one light source and at least one aperture for at said least one light detector, wherein each of said at least one light detector and at least one light source are optically isolated from each other inside said casing. The portable biometric device contains all the components installed in the casing. The casing is a compact casing, such as wrist size casing or other wearable casing configured to be installed with a strap to a user.

The optical components at least one light source and at least one light detector are located on the circuit board, preferably on the same side of the circuit board. They are operatively connected to the circuit board so that they may be controlled and operated by the control unit of the device. The at least one light source and at least one light detector are separate components on the circuit board, i.e. preferably they are not present as a module and they may be optically isolated from each other. The circuit board is in the casing.

In one embodiment the portable biometric device comprises at least one lens optically connected with said at least one light source and at least one lens optically connected with said at least one light detector. "Optically connected" as used herein refers to an arrangement wherein a lens and a light source, or a lens and a light detector are positioned so that the light emitted by the light source exits through the corresponding lens, or a light detected by the light detector enters through the corresponding lens. In practice this means that the corresponding lens is placed on top of the light source or the light detector, either directly or with a gap between, and with adhesive or without adhesive. The lens refers to a transparent piece, which may be for example made of plastics or glass. The lens may or may not refract light. The lenses protect the optical components inside the casing preventing water and/or dust entering the casing. The lenses may be arranged to refract the emitted light reflected from the user's skin so that it will be detected in optimal angle and intensity. In one example the lens is converging. In one example the surface of a lens is flat i.e. not refracting. In one example the lenses are placed in a corresponding aperture in the casing which is tight enough to retain the lens. Adhesive may be used to enhance the adhesion. In one example the lenses are placed in a corresponding aperture in the casing from inside the casing and the inner side of a lens is wider than the outer side of the lens so that the outer side fits the aperture and the wider inner side prevents the lens from slipping through the aperture (see FIG. 4).

"Optically isolated" as used herein refers to an arrangement wherein each of at least one light sources and each of at least one light detectors are arranged in separate optically isolated compartments, which are not optically connected. This means that the leakage of light from one compartment to another inside the casing has been prevented by using suitable isolating material between the compartments, such as the gasket or the sealing plate described herein, which terms may be used interchangeably. Said sealing plate has at least corresponding apertures for the optical components as are present in the casing. The only light path from such an optically isolated compartment preferably leads outside the casing through an aperture in the casing, which aperture is arranged to be positioned to the skin of the user when the biometric monitor is in use.

In one embodiment the optical sensor contains adhesive between said at least one light source and said at least one lens optically connected to said light source, and/or between said at least one light detector and said at least one lens optically connected to said light detector. This enhances the optical connection between the light source and the light detector and the corresponding lenses because there are no optical boundaries between air and the lens inside the casing or between air and the light source or air and the light detector. Without the adhesive there would be two air/solid boundaries in the light path which may reduce the optical properties of the sensor, e.g. by causing reflections. The use of the adhesive maximizes the signal level thus enhancing the intensity of the light. The distance between the light source or the light detector and the corresponding lens does not change for example if the device is subjected to vibration. This provides for example a lower noise level. The optically isolated compartment may be filled completely with the adhesive, or an amount of adhesive may be applied which is enough to optically connect the light source and/or light detector and the corresponding lens.

The type of the adhesive may be selected to be compatible with the materials used in the lenses and in the light source and the light detector. In one example the refractive index of hardened adhesive is substantially the same as the refractive index of the lens to obtain minimum loss at the boundary.

In one embodiment the optical sensor contains adhesive on said at least one light source and/or on said at least one light detector, said adhesive forming a transparent layer on said at least one light source and/or on said at least one light detector. This adhesive layer acts as a lens on the light source or the light detector. No further separate lenses, such as plastic of glass lenses, are required and they are not present.

The aperture in the sealing plate may be filled completely with the adhesive, and further the aperture in the casing may also be filled with the adhesive, i.e. the surface of the adhesive is substantially on the same level as the outer surface of the casing. This makes the optical sensor completely waterproof. Further there are no optical boundaries between air and the lens inside the casing or between air and the light source or air and the light detector.

In general the light source and the light detector are not in direct contact with the skin of the user, but they may be in the distance of about 0.5-3 mm from the skin or the outer surface of the casing which will be against the skin during the use. As described above there may be separate lenses, with or without adhesive, or adhesive only without lenses between the outer surface of the casing and the light source and the light detector. The casing may be made of metal, which provides rigid support for the components of the wrist device, and facilitates the grounding of the device with user's skin. When metallic housing or casing is used, it may be desired to keep the optical components at a certain distance from the casing, for example to avoid direct contact of the sensitive components with the casing or the user's skin. Therefore in one embodiment the light source and the light detector are not directly inside the apertures of the casing, but at said distance 0.5-3 mm from the outer surface of the casing, for example 1-3 mm, 2-3 mm, or 1-2 mm. Therefore the light isolating means are required inside the casing to optically isolate the light detector(s) and light source(s) from each other. In such case the casing has more particularly at least one aperture for enabling a light path for said at least one light source and at least one aperture for enabling a light path for said at least one light detector. The "light path" refers to a path through the apertures in the casing where the light may travel, either from the light source to outside the casing or from outside to the light detector.

In one embodiment the adhesive comprises epoxy adhesive. Epoxy is the cured end product of epoxy resins, as well as a colloquial name for the epoxide functional group. Epoxy is also a common name for a type of strong adhesive used for sticking things together and covering surfaces, typically two resins that need to be mixed together before use (two-part or two-component epoxy adhesive). Epoxy adhesives are a major part of the class of adhesives called "structural adhesives" or "engineering adhesives" (that includes polyurethane, acrylic, cyanoacrylate, and other chemistries.) Epoxy adhesives are better in heat and chemical resistance than other common adhesives. In general, epoxy adhesives cured with heat will be more heat- and chemical-resistant than those cured at room temperature. The strength of epoxy adhesives is degraded at temperatures above 177° C. Some epoxies are cured by exposure to ultraviolet light. Such epoxies are commonly used in optics, fiber optics, and optoelectronics. In one example the adhesive is a two part epoxy adhesive, wherein two compounds are combined and mixed prior to use.

In one embodiment the light source has a cavity containing said adhesive. For example a specific type of LED may have such a cavity. In one embodiment the light source is a LED.

In one embodiment the optical sensor does not contain adhesive between said at least one lens and said at least one light source, and/or between said at least one lens and said at least one light detector. This provides an effect of enhanced shock resistance as the optical components, i.e. the lenses and the light source and the light detector, do not form a continuous solid piece from the circuit board to the casing. An increased shock resistance may be beneficial in a portable device used for example in sports, such as a portable heart rate monitor. Also the device is simpler to manufacture when no adhesive is used in the optical components, which saves time and costs. There is a gap between said at least one lens and said at least one light source, and/or between said at least one lens and said at least one light detector, which gap may be for example in the range of 0.1-1 mm, such as 0.2-0.8 mm. A larger gap is challenging for the optical properties of the sensor. A smaller gap on the other hand may impair the mechanical properties of the device, for example the shock absorbing properties. Similar distances between the optical components and the lenses may also be used in the embodiments wherein adhesive is used.

The sealing plate, which may be also called gasket, is generally made of elastic material, i.e. the sealing plate is elastic sealing plate. The elasticity compensates any inaccuracies or protruding parts in the components made into contact with the sealing plate, for example components on the circuit board. The construction will be light proof, air proof and water proof. The elastic sealing plate may also play a role in providing enhanced shock absorbing properties. The sealing plate may be a single piece. It may have a thickness in the range of 0.3-2.0 mm, for example in the range of 0.3-1.0 mm, or more particularly 0.3-0.7 mm. In one example the thickness of the sealing plate is about 0.35 mm. The sealing plate is prepared in advance, i.e. it is prefabricated. The sealing plate is configured to fit into the casing. As it is used for optically isolating the optical components it should be non-transparent or opaque, for example black. In one embodiment the sealing plate comprises elastomer. In one embodiment the sealing plate comprises microcellular elastomer. An elastomer is a polymer with viscoelasticity (having both viscosity and elasticity) and very weak inter-molecular forces, generally having low Young's modulus and high failure strain compared with other materials. The term, which is derived from elastic polymer, is often used interchangeably with the term rubber, although the latter is preferred when referring to vulcanisates. Each of the monomers which link to form the polymer is usually made of carbon, hydrogen, oxygen and/or silicon. Elastomers are amorphous polymers existing above their glass transition temperature, so that considerable segmental motion is possible. At ambient temperatures, rubbers are thus relatively soft and deformable. Examples of elastomers include unsaturated rubbers, such as natural polyisoprene, synthetic polyisoprene, polybutadiene, chlorophene rubber, butyl rubber, styrene-butadiene, or nitrile rubber. Other examples of elastomers include saturated rubbers, such as ethylene propylene rubber, epichlorohydrin rubber, polyacrylic rubber, silicone rubber, fluorosilicone, fluoroelastomers, polyethylene block amides, chlorosulfonated polyethylene or ethylene vinyl acetate. In one embodiment the sealing plate comprises synthetic rubber, for example neoprene. Neoprene or polychloroprene is a family of synthetic rubbers that are produced by polymerization of chloroprene. Neoprene exhibits good chemical stability, and maintains flexibility over a wide temperature range. In one embodiment the sealing plate comprises foam rubber. Foam rubber (also known as cellular, sponge, or expanded rubber) refers to rubber that has been manufactured with a foaming agent to create an air-filled matrix structure. Commercial foam rubbers are generally made of either polyurethane or natural latex. In one example the elastic material comprises microcellular urethane.

The sealing plate may be die-cut, e.g. from a larger sheet, to form the desired shape and the apertures. The sealing plate may or may not contain adhesive. In one embodiment the sealing plate contains adhesive on one or both sides. In one embodiment the sealing plate is provided with adhesive on one or both sides with a release liner on the adhesive, for example a film or a paper coated with release agent, such as silicone. The adhesive may be pressure-sensitive adhesive (PSA). Pressure sensitive adhesive, also known as self-stick adhesive, forms a bond when pressure is applied at room temperature. PSA labels can be adhered to most surfaces through an adhesive layer without the use of a secondary agent such as solvents or heat to strengthen the bond. Examples of pressure sensitive adhesives include emulsion and water based PSAs, solvent based PSAs and solid PSAs. In one embodiment the pressure sensitive adhesive comprises UV hot melt adhesive. Prior to use of the prefabricated sealing plate the release liner is removed to uncover the adhesive, whereupon the sealing plate may be attached onto target, such as onto the circuit board or the casing. When a sealing plate with adhesive is used the sealing plate may be attached with high accuracy and it remains on the target during the assembly. The adhesive, especially when on both sides of the sealing plate, will also stabilize the final construction. The use of previously applied adhesive, such as pressure sensitive adhesive with a release liner, simplifies the process and saves time and money. If adhesive is used it may stabilize the sealing plate with the other parts of the optical sensor thus enhancing the optical isolation and mechanical properties of the setup.

In one embodiment the optical sensor contains one light detector and two light sources, i.e. there is only one light detector and only two light sources, which may be arranged in line, the light detector being in the middle.

One embodiment provides a method for manufacturing an optical sensor, the method comprising providing at least one light source and at least one light detector installed on a circuit board, a casing having at least one aperture for said at least one light source and at least one aperture for said at least one light detector, and a sealing plate arranged to fit between said casing and said circuit board, said sealing plate having at least one aperture for said at least one light source and at least one aperture for said at least one light detector, and combining said circuit board, said sealing plate and said casing so that said at least one light source and said at least one light detector fit to the apertures in the sealing plate for optically isolating said at least one light source and said at least one light detector from each other inside said casing. More particularly the circuit board and the sealing plate are placed inside the casing.

The sealing plate may be placed first inside said casing, or it may be placed first onto said circuit board, before combing the parts. In one embodiment the sealing plate contains adhesive on at least one side. In one embodiment the sealing plate contains adhesive on both sides. In one embodiment a sealing plate with adhesive on both sides, preferably covered with a release liner, is provided. In one embodiment a release liner on one side is first removed, and the sealing plate is attached onto the circuit board. In one embodiment a release liner on one side is first removed, and the sealing plate is attached onto the casing, more particularly onto the inner side of the bottom of the casing. In any case the sealing plate is positioned in such way that the corresponding apertures fit to the optical compounds and/or corresponding lenses or apertures. In one embodiment the method comprises providing the sealing plate with adhesive on one or both sides with a release liner on the adhesive, and removing the release liner prior to combining the sealing plate with said circuit board and/or said casing.

In one embodiment a further stabilizing device is provided, in general a work-holding or support device, for example a jig or a fixture, which may contain one or more guiding parts, for example protruding parts, such as pins, adapted to fit to apertures and/or edges of the sealing plate. In one embodiment the method comprises positioning the sealing plate onto the stabilizing device, preferably with the release liner still attached on the side which will be in contact with the stabilizing device, exposing the adhesive on the opposite side of the sealing plate, and positioning the part to be attached with the sealing plate onto the sealing plate on the stabilizing device in such way that the sealing plate will be attached onto said part. The stabilizing device may contain guiding means, which guide the sealing plate and the part to be attached, such as circuit board or the bottom of the casing, together to obtain accurate alignment of the parts. The use of such stabilizing and guiding means reduces the possibility of human error in the assembly process, and the parts will be combined with high accuracy and reproducibility. When a two-sided adhesive on the sealing plate is used, the release liner on the other side is next removed and the corresponding part is combined with the sealing plate.

In one embodiment the method comprises applying adhesive onto said at least one light source and onto said at least one light detector. Further the adhesive is let to cure In one embodiment the method comprises further providing at least one lens for at least one light source and at least one lens for at least one light detector, and placing said lenses to the apertures in the casing. The lenses may be placed to the apertures from outside the casing or from inside the casing.

In one embodiment the method comprises stabilizing the parts, such as said circuit board, said sealing plate and said at least one light source and said at least one light detector substantially for the time the adhesives takes to cure. This may be carried out by using means for stabilizing the assembly formed by said parts, for example a jig or the like. In one example the means for stabilizing the components comprises an arrangement having a slot for the assembly. The assembly is inserted to the slot wherein the parts are pressed together. The parts are not allowed to move in the slot. The stabilization of the assembly is especially important when the device includes parts which cause tension, for example springs or elastic material. In one example charging clips may cause such a tension during the assembly especially if they have metal springs for ensuring a proper contact to the circuit board. Also the adhesive may either shrink or expand during curing. Without stabilization the assembly might move during the curing thus causing poor adhesion and problems in the positioning of the parts. The stabilization keeps the volume of an aperture constant. The curing time of the adhesive depends on the type of adhesive used, and it may range for example from about an hour to up to 12 hours. For example two-component epoxy adhesive may take about 7-10 hours to cure, for example about 8 hours.

There may be air bubbles in the adhesive, for example formed during the mixing of the adhesive. These air bubbles would deteriorate the optical properties of the final optical sensor, so it is desired to remove as much of the air bubbles as possible before the adhesive is cured, or at least guide the air bubbles to an area in the adhesive part wherein they are not directly in the light path.

In one embodiment the method comprises removing air bubbles from the adhesive before applying the adhesive. In one example this is carried out by using vacuum. A portion of the adhesive is subjected to vacuum for a time long enough to remove a substantial amount of air bubbles from the adhesive, for example at least 50% of the bubbles, or 60%, or 70%, or 80%, or 90%, or 95%, or 98%, or 99% or substantially 100%. This time may be for example in the range of 1-60 minutes. After the removal of air the adhesive may be applied onto the optics of the device. In one example the order of assembling the device facilitates the removal of the air bubbles from the adhesive. For example after placing said sealing plate inside said casing and the casing is positioned so that the apertures face up. Then the adhesive is applied to the apertures in the sealing plate. Also the circuit board is positioned so that said at least one light source and said at least one light detector substantially face up, applying adhesive onto said at least one light source and said at least one light detector, arranging a delay for a time enough for letting the adhesive to settle, turning the circuit board upside down and placing it onto the sealing plate so that said at least one light source and said at least one light detector fit to the apertures in the sealing plate for joining the corresponding adhesives, and letting the adhesive to cure. When the adhesive is settling, the air bubbles will rise to the surface of the adhesive and are released to the ambient air, or at least the air bubbles are guided to rise to a part of the adhesive which is not in the direct light path, for example they are guided to the edge of the light path. This may be accomplished by positioning the circuit board during the settling of the adhesive in such way that the bubbles will rise to the edge of the adhesive. The time the adhesive takes to settle may vary depending on the adhesive, and is may be generally about the same as the open time or the working time of the adhesive. Open time refers to a time period wherein the adhesive is still in liquid form and is workable. For example a super epoxy may have a working time of about 30 minutes. The time the adhesive takes to settle may be for example in the range of 1-60 minutes. Curing time refers to the time required for the adhesive to set into a solid form.

The adhesive may be injected to the aperture to be glued by using any suitable means for dosing the adhesive. The means for dosing the adhesive may comprise a simple manual device such as a syringe or the like, or a more automated injection device containing means for dosing a desired dose of the adhesive, which may further contain any means for measuring the properties of the adhesive, for example the amount of the adhesive or any optical properties of the adhesive. The presence of any air bubbles may be for example detected by using such as optical meter.

In one embodiment the method comprises providing at least one aperture in the circuit board for applying the adhesive, and injecting the adhesive from the opposite side of the circuit board through said at least one aperture onto said at least one light source and/or onto said at least one light detector, preferably after the circuit board and the sealing plate have been combined. In one example there is at least one such aperture for at least one light source and at least one such aperture for at least one light detector, each aperture leading to one optically isolated compartment. The "opposite side of the circuit board" refers to the side opposite to the side wherein the optical components are located. There may be further other apertures for letting the air exit as the adhesive enters. In this case the circuit board, said sealing plate and said casing may be already combined before applying the adhesive. Therefore the injected adhesive will fill the empty space efficiently. This embodiment may be used with the lenses as described above or without the lenses as well. The assembly may be stabilized during the injection, as described above. One embodiment provides a portable wrist device manufactured with said method. The method of injecting the adhesive through said aperture in the circuit board may be detected from the final product as the aperture and the hardened injected adhesive are visible.

Figure 1A:
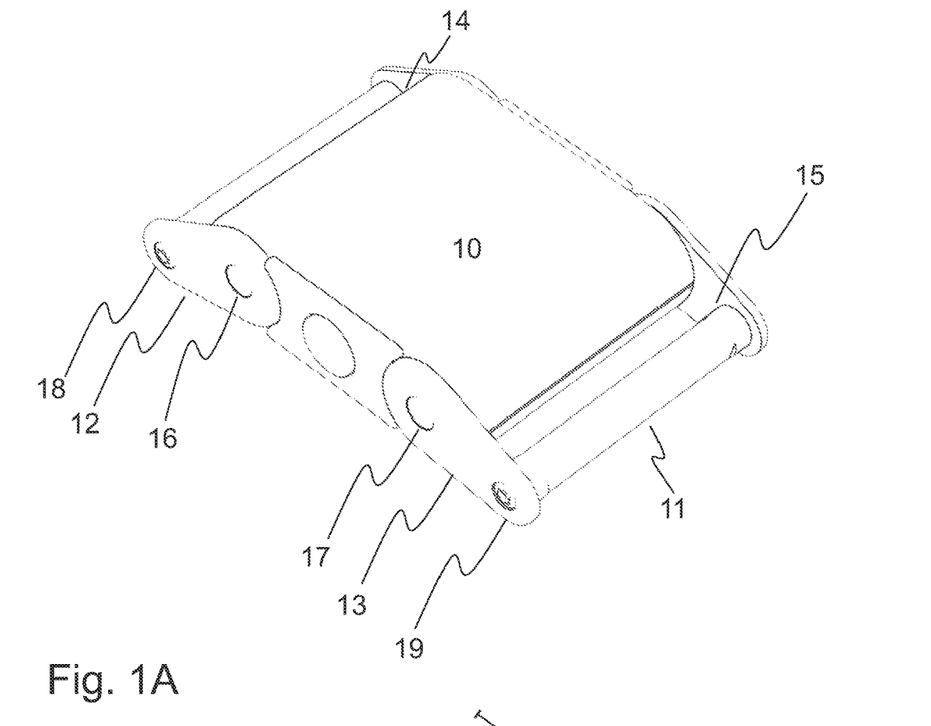
FIGS. 1A and 1B show the outer parts of a biometric monitor.
Figure 1B:
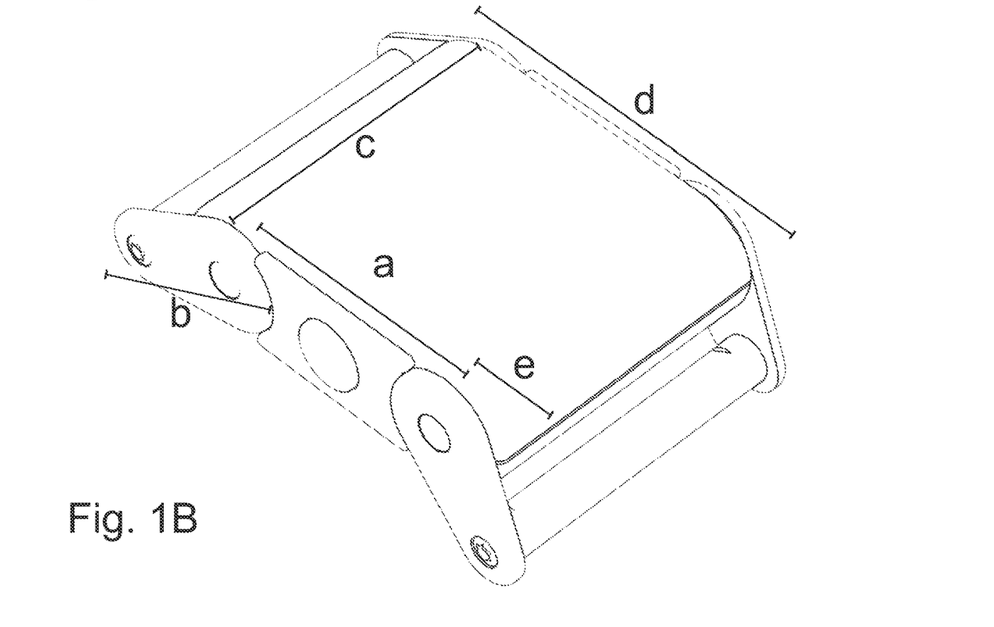
Figure 2A:
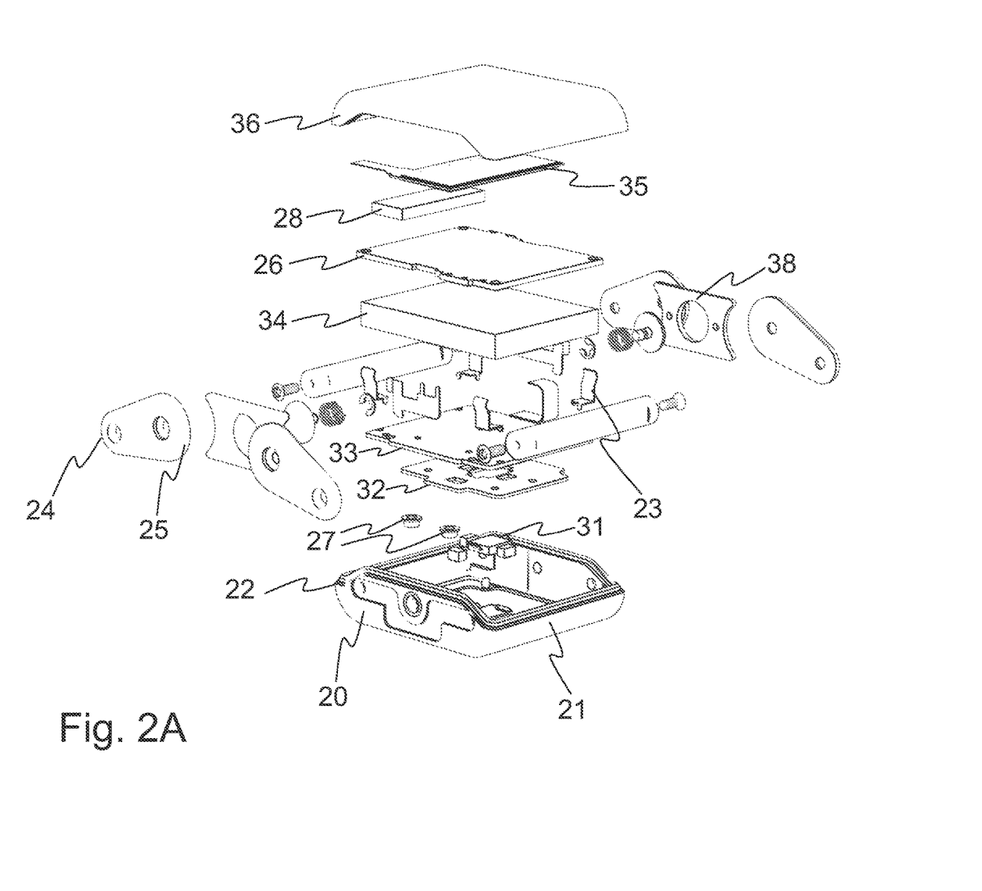
FIG. 2A shows an exploded view of a biometric monitor.
Figure 2B:
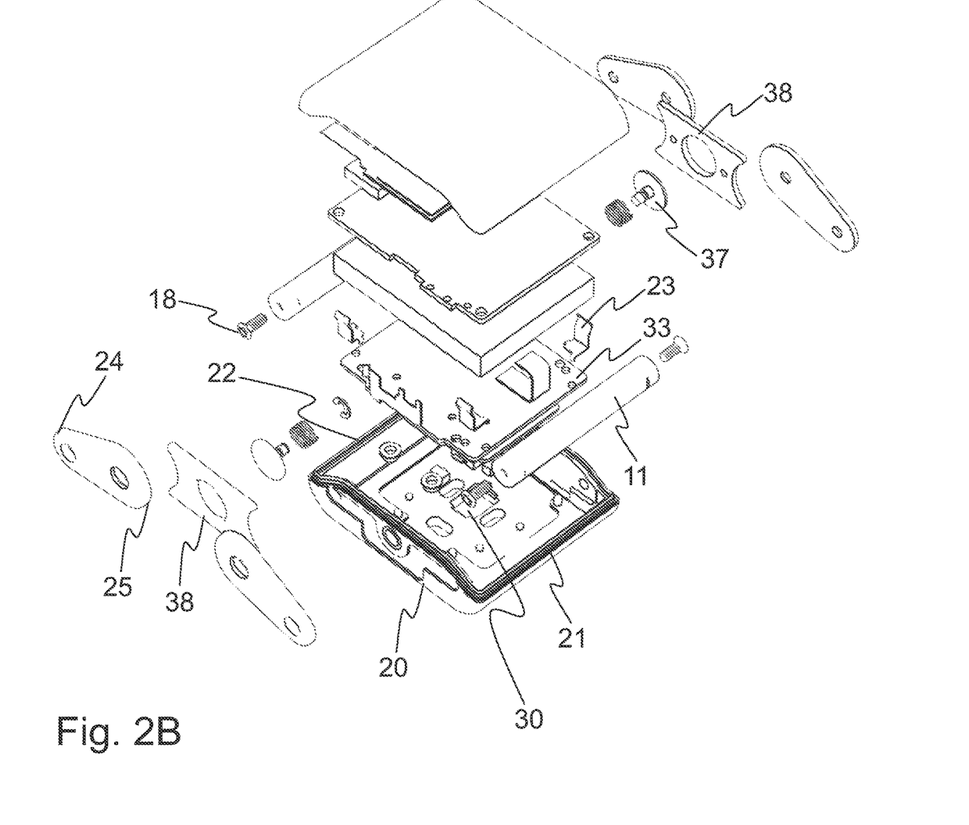
FIG. 2B shows the view from a different angle
Figure 3A:
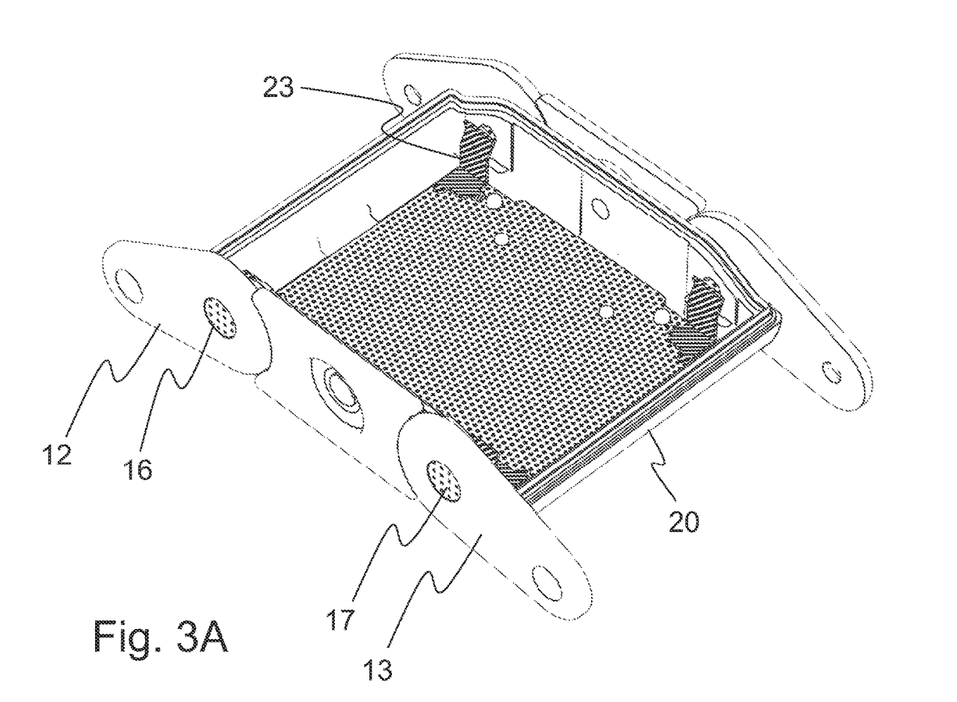
Figure 3B:
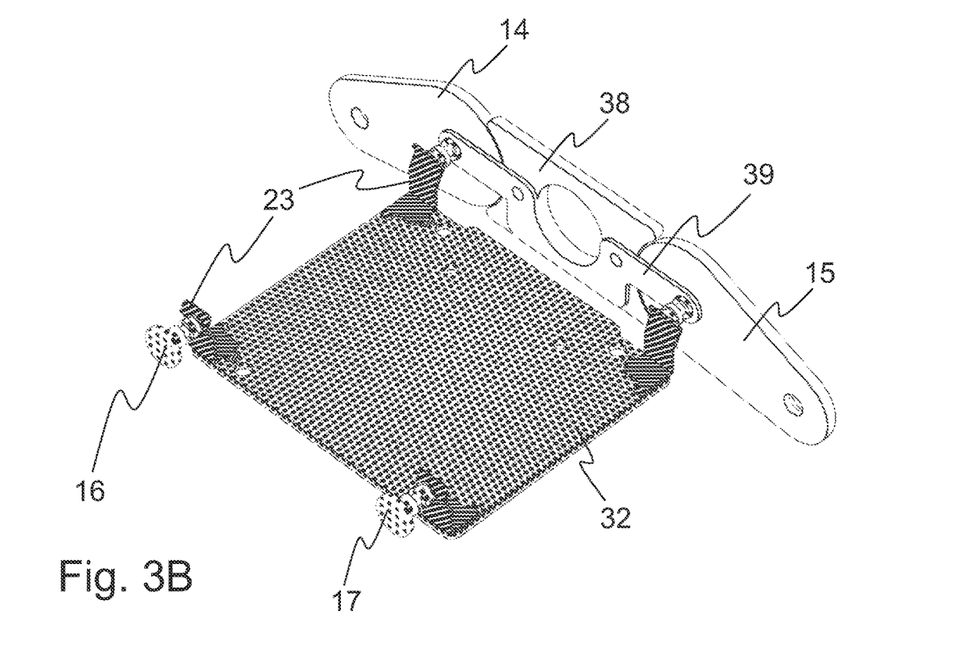
FIG. 3B shows the same view without the spacer elements and other parts on the other side

An example of a biometric monitor is illustrated in the FIGS. 1-3. One example provides a portable biometric monitor 10 comprising a housing 20 having a first end 21 and a second end 22, one or more processors, memory, one or more biometric sensors, and an interface operatively connected together. The biometric monitor may be a wearable monitor used as a sport or fitness monitor, health monitor or the like.

The main parts visible outside in one example are shown in FIGS. 1A and 1B. The casing or housing 20 of said biometric monitor 10 may generally have a shape and the size of a wrist watch, for example it may be have a length d in the range of 20-60 mm, for example in the range of 25-40 mm. It may have a width c in the range of 15-60 mm, such as 15-40 mm, for example in the range of 20-60 mm, in the range of 25-35 mm, or in the range of 25-30 mm. The shape of the casing in generally substantially flat, having a thickness in the range of 3-15 mm, for example in the range of 5-10 mm, or in the range of 8-15 mm. The thickness of the wall of the casing may be in the range of 0.7-2.5 mm, such as 1.1-2.25 mm, or 0.8-1.5 mm. In one example the casing is angular in shape, for example substantially square. The edges may be rounded. The casing may also have an oval or round shape, or a combination of the shapes mentioned herein. The first end 21 and the second 22 end may be defined according the direction of the casing when attached to the user or to the strap, especially in the case wherein the shape of the casing is substantially round. In one example the length of the casing is larger than the width thereof. The casing may also be called as the body or frame of the biometric monitor. The casing may be made of metal, or it may have a body or frame made of metal. This enables mechanically reliable joints with the pivots or axles. Examples of metal include steel, stainless steel, titanium, light alloys and the like. The casing may also be made of plastics. A casing made of plastics may be used to provide products having decreased weight, to save in the manufacturing costs and to facilitate the manufacturing process. In such case the pivots may be anchored to the casing for example by using metal lockwashers inside the casing, and by using a connecting part 39 made of metal arranged to receive the pivots, usually arranged to receive two pivots at the same side of the monitor. The connecting part 39 is grounded via the pivots, and it also grounds the side plate 38.

The casing may be connected to a wearable strap for attaching the portable biometric monitor to a user, for example to a wrist of the user, the strap comprising a first end and a second end. The strap may be continuous including only one strap part, or it may be discontinuous including at least two parts which may be connected by a buckle. In one example the strap contains two parts connected by a buckle. The strap may have a width of substantially the width of the casing, or little less, such as 0.5-2 mm narrower than the width of the casing. The thickness of the strap may be in the range of 0.5-3 mm. In one example the strap is made of stretchable or elastic material, such as canvas, rubber, or combinations thereof. In one example the strap is made of non-stretchable material, such as plastics, leather, metal, or combinations thereof. Examples of metal include steel, stainless steel, titanium, light alloys and the like.

In one example the strap is a wrist strap. Other examples of the straps include forearm straps, ankle straps, forehead straps, tights straps, leg straps, arm straps and neck straps. However, the dimensions used in the examples herein are optimized for wrist straps for different wrist sizes.

The biometric device includes at least an optical sensor as a biometric sensor. Other examples of biometric sensors include a temperature sensor, a potential sensor, a sound or an ultrasound sensor, a galvanic skin response sensor (GSR), an EKG sensor, an EMG sensor, a wavelength sensor, and a motion detector. The biometric monitor may contain one or more different biometric sensor(s), for example two, three or four sensors. Also other sensors may be included, such as a GPS sensor, a magnetometer, or a motion detector, for example inertia, gyro or accelerometer. Usually the biometric sensor is located on the skin side or the user side of the device.

Examples of possible physiological parameters to be monitored with the one or more biometric sensors in addition to heart rate include body temperature, blood pressure, blood flow, skin conductivity, tissue impedance, heart rate variability, motion, sleep, stress, fitness level, recovery level, effect of a workout routine on health, and caloric expenditure.

In one embodiment the portable biometric monitor is a heart rate monitor, or a pulse monitor comprising an optical sensor, or an optical detector. The optical heart rate monitoring may be based on light scattering monitoring. In general an optical sensor includes one or more light or illumination sources for emitting light and one or more light or illumination detectors for detecting the light scattered or reflected from the user's body. Examples of the light sources include LED, laser and the like. Examples of the light detectors include photodiodes, phototransistors and the like. In one example the optical sensor comprises one light source and one light detector. In one example the optical sensor comprises two light sources and one light detector between the light sources, preferably all in a line. In one example the optical sensor comprises three light sources and two light detectors between the light sources, preferably all in a line. The light source(s) may emit light at one or more wavelength(s) or wavelength ranges. The light detector(s) may detect light at one or more wavelength(s) or wavelength ranges. Examples of such wavelength ranges include green spectrum, blue spectrum, red spectrum, and infrared spectrum. The light source(s) or the light detector(s) may further have a filter for filtering out undesired wavelengths. Examples of specific light sources having a specific wavelength range include green LED, blue LED, red LED, infra red LED, near infra red LED and combinations thereof. In general green light is suitable for the measurement of superficial blood flow in skin. Light with wavelengths between 500 and 600 nm (the green-yellow region of the visible spectrum) exhibits the largest modulation depth with pulsatile blood absorption. IR or near-IR wavelengths may be better for measurement of deep-tissue blood flow, such as blood flow in muscles.

In one example the light source is a green LED. A green LED has much greater absorptivity for both oxyhaemoglobin and deoxyhaemoglobin compared to for example infrared light. Therefore, the change in reflected green light is greater than that in reflected infrared light when blood pulses through the skin, resulting in a better signal-to-noise ratio for the green light source. Infrared light may be used also to measure skin's moisture content on the absorption of infrared light by the dermis, or for other purposes.

The optical sensor is mounted at the bottom of the monitor body, on the skin side of the user. The optical sensor may form a protrusion of about 0.5-2 mm from the bottom of the monitor for anchoring the sensor to the skin, generally the protrusion having curved sides. Usually this is on the opposite side of the monitor body in relation to the display. FIG. 2B illustrates holes for the optical sensor in the bottom of the housing 20.

More precisely the optical heart rate monitoring is implemented by irradiating the skin of the user with visible or infrared light generated by said light source. The light source is generally arranged in close contact with the skin of the user. A light detector is arranged also in close contact with the skin in a nearby location and it is arranged to detect and measure the light resulting from reflection, absorption and/or scattering by the skin. The variations in said detected and measured values allow the measurement of the flow of oxy- and deoxyhemoglobin and the expansion of blood vessels. A photoplethysmogram (PPG) may be obtained. This enables for example oxymetric and pulsometric measurements, which may be further used to define the heart rate of the user.

In addition to heart rate, an optical sensor may be configured to monitor the user's respiration, heart rate variability, oxygen saturation (SpO2), blood volume, blood glucose, skin moisture and/or skin pigmentation level.

In one example the portable biometric monitor, or the electronics thereof, is grounded to the metallic pivot from inside the housing with grounding elements. This is necessary especially is biometric monitor using radiofrequency communication to transfer data or otherwise exchange information wirelessly with another device or entity, and/or if such biometric monitor uses radiofrequency sensing such as GPS for location detection. In one example the portable biometric monitor is grounded to the metallic pivot via a spring member 23 as the grounding element, as illustrated in FIGS. 3A and 3B. The spring member 23 protrudes from the electronics module to a location of the metallic pivot or axle inside the casing and touches the pivot or axle to obtain an electrical contact with it. The spring force directed to the pivot maintains the electrical contact. No soldering or the like is required to establish a reliable contact, which saves time and costs during the assembly of the device, or in case when disassembly is required, for example during a service. In one example the grounding elements are integral parts of a metallic bottom plate, which is located between the electronics, e.g. a circuit board, and the biometric sensor. In one example the grounding elements are separate elements, which are connected to a larger grounding part, such as a metallic bottom plate. An example of such bottom plate is presented in FIGS. 3A and 3B as spotted hatching while the grounding elements 23 are presented as dashed. There may be one, two, three or four grounding elements, for example two at the both sides of the housing at one end of the housing. The bottom plate may be used for example if the circuit board is thin and/or flexible and needs support. If the circuit board is rigid, it may replace the bottom plate. The thickness of the rigid circuit board may be in the range of 0.4-2 mm, for example in the range of 0.6-1.0 mm.

The biometric monitor generally includes one or more processors, memory, one or more biometric sensors, an interface, and optionally a display arranged to present information, operatively connected together. The biometric monitor naturally contains a power source, for example a battery or a solar cell. The one or more processor(s) is/are configured to process the biometric information which is detected and measured by the one or more sensors, to determine an output from the measurement. The one or more processor(s) is/are usually comprised in a control unit or in means for controlling the biometric monitor. The determined information may be outputted to a display, or the information may be sent to an external device wirelessly connected to the biometric monitor, for example by using Bluetooth, WiFi, cellular or any other suitable wireless technology. In such case the biometric monitor contains means for wireless communication, such as a transmitter and a receiver configured to communicate with the external device. One or more of the one or more processors, the memory, one or more biometric sensors, the interface, and the display arranged to present information are usually implemented as one or more electronic circuit boards or modules. These parts can be seen in the explosion views of FIGS. 2A and 2B, all installed into a casing. The device may also contain audio means for outputting and/or inputting sound, for example as a part of the user interface.

The display may use one or more of any of the suitable display technologies including LED, LCD, AMOLED, E-Ink, Sharp display technology, graphical display, and other suitable display technologies. This display may be used to present data acquired or stored locally on the device or data acquired remotely from other devices or Internet services.

The external device may be a mobile terminal, for example a handheld device such as a mobile phone or a tablet, or a computer, for example as a portable computer or any other computer, or any other suitable external device. The information may be processed and/or displayed in the external device, for example the information may be collected, saved, processed and analyzed. Other types of information may also be combined with the measured biometric information, such as geographic information for example obtained from a GPS system in the device itself or in the external device, time information, temperature information, and the like. The other information may be measured using the same device or the other information may be obtained from another source or device, such as the external device. The combined information may be processed to a presentable form, for example to present statistical information as graphs or tables.

The interface may comprise a user interface for indicating the state of one or more data types measured and/or analyzed. The user interface may also include one or more physical buttons and/or a touch sensitive screen as means for controlling the device and/or interacting with it, or a combination thereof. The interface may also comprise means for communicating with an external device by using wireless technology. The interface may also comprise means for presenting information on a display. FIGS. 2A and 2B show examples of physical buttons between the pivots on the sides of the housing. The buttons contain a spring for enabling non-locking key functionality. In this example there is a further side plate 38 between the spacer elements 12, 13, 14, 15, wherein this side plate 38 contains a hole for receiving the button 37 and has the same thickness as the spacer elements 12, 13, 14, 15. This enables providing the button on the same level as the spacer elements, and the button may be pressed inwards. Therefore the button does not extend from the side of the monitor and it also does not reserve space inside the housing.

EXAMPLES

The FIGS. 1A and 1B illustrate an exemplary embodiment of a biometric monitor 10 as a wrist device having an optical sensor at the bottom of the housing 20. The housing 20 has a length d of about 32 mm, and a width c of about 26 mm (the spacer elements are not included). The distance a between the pivot locations between the first end of the housing and the second end of the housing is about 21.5 mm. The distance between the center of the pivots 17, 19 in the first end 24 and in the second end 25 of the spacer elements 12, 13, 14, 15 is about 10 mm, the length b of the spacer elements being about 17 mm. The distance e of a pivot 17 center from an end 21 of the housing 20 is about 5 mm.

In this example the spacer elements and the pivots are made of steel, and the housing 20 and the axles 11 are made of plastics. The side plate 38 between the spacer elements and the buttons 38 embedded therein are made of steel. The side plate has curved ends for receiving the corresponding ends 25 of the spacer elements 12, 13, 14, 15. The side plate is attached by pegs to a metallic connecting part 39 which also has protruding parts having holes for receiving the two pivots on the same side of the monitor (FIG. 3B). This part anchors most of the metallic parts enabling the housing to be made of plastics.

An assembly of the monitor is illustrated in FIGS. 2A and 2B. On the bottom there is a housing 20 having apertures 30 for receiving the parts of the optical sensor 31, the two light sources and one light detector in line and one light source on the side. The casing 20 has corresponding apertures for each of said optical components as seen in FIG. 2B. The parts of the optical sensor are attached to a circuit board 33. An opaque sealing plate or a gasket 32 prevents a leakage of the light inside the device. Also the sealing plate 32 has corresponding apertures for each of said optical components as seen in FIG. 2A. The metallic grounding members 23 are attached to the circuit board 33 to enable the grounding of the system. The spring-like grounding parts 23 are arranged to be pressed against the inner ends of the pivots 16, 17, to enable electrical contact for grounding, as seen in the FIGS. 3A and 3B. Above the circuit board there is a battery 34 and a board 26 containing the electronics. The battery is connected to charging clips 27 at the bottom of the monitor. The display 35 is located on top of the electronics module and it is covered by a partly transparent display cover 36, which is the topmost part of the assembly. In the illustrated example there is also a GPS antenna 28 located near the display 35 below the cover 36.

There is one button 37 at both sides of the monitor. The buttons 37 include a spring and a metallic lockwasher as fastening means inside the housing 20. The pivots are fastened using similar lockwashers inside the housing.

Figure 4:
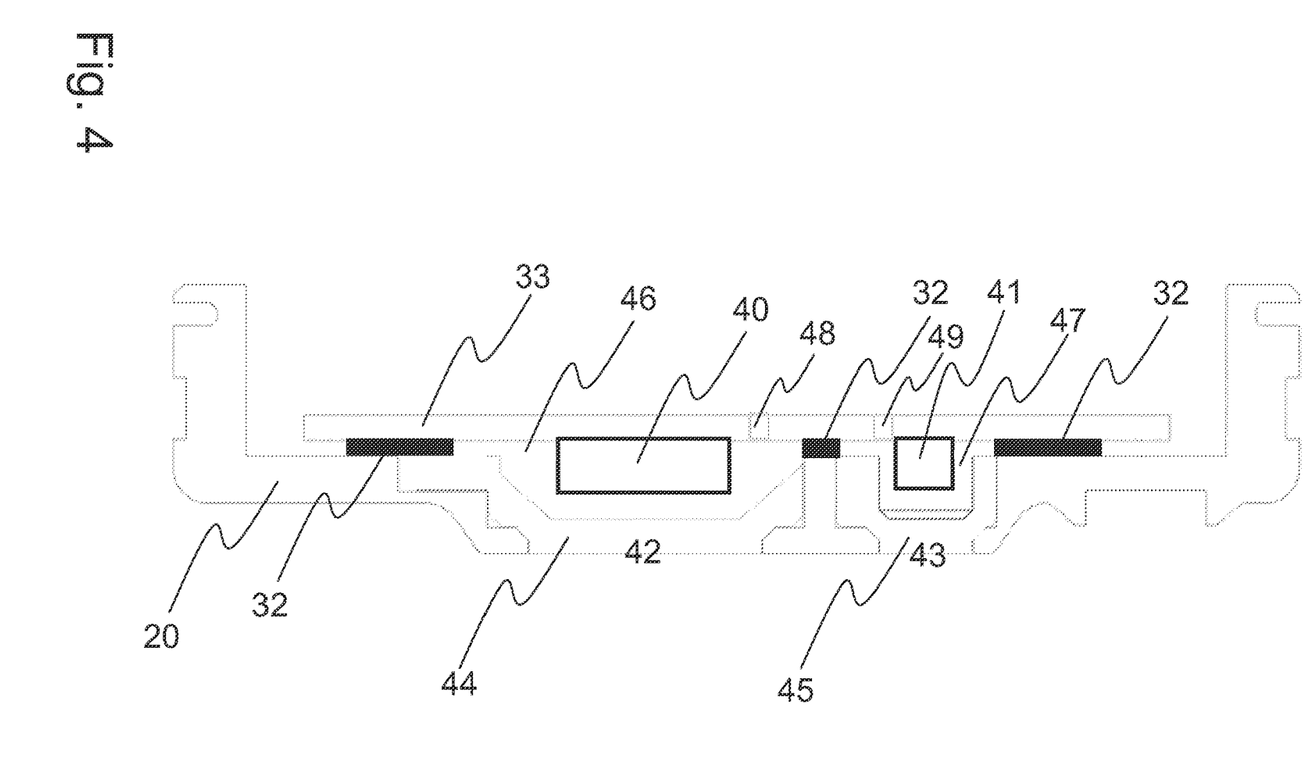
FIG. 4 shows a cross-sectional view of an exemplary implementation of an optical sensor

A cross-sectional view of an exemplary implementation of an optical sensor is illustrated in FIG. 4. The optical sensor forms a bump in the bottom of the casing 20. The casing wall has a thickness of 1.15 mm in general, except 2.25 mm at the location of the bump. The casing 20 has apertures 42, 43 containing lenses 44, 45. A photodetector 40 and a LED as a light source 41 are installed on a circuit board 33 having a thickness of 0.6 mm. The distance between the circuit board 33 and the bottom of the casing is 2.6 mm. Between the photodetector 40 and the lens 42 there is a space 46, which may or may not be filled with adhesive. Similarly, between the light source 41 and the lens 45 there is a space 47, which may or may not be filled with adhesive. The compartments including the space 46 and the lens 44, and the space 47 and the lens 45 are optically isolated from each other with the gasket 32, shown as black. In one example there are apertures 48, 49 for injecting adhesive to the corresponding spaces 46, 47.

Figure 5:
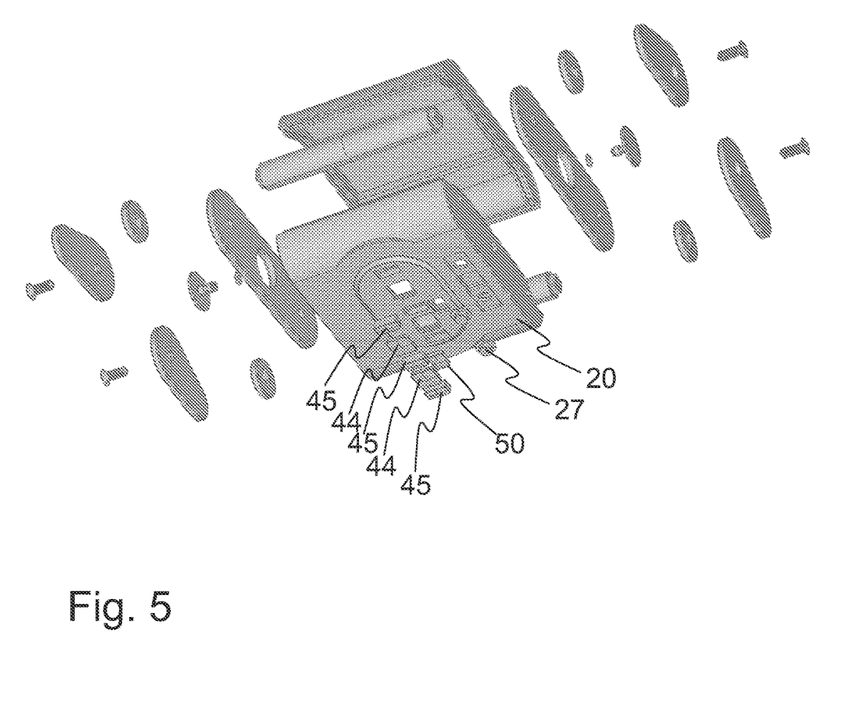
FIG. 5 shows an exploded view of a biometric monitor from outside
Figure 6:
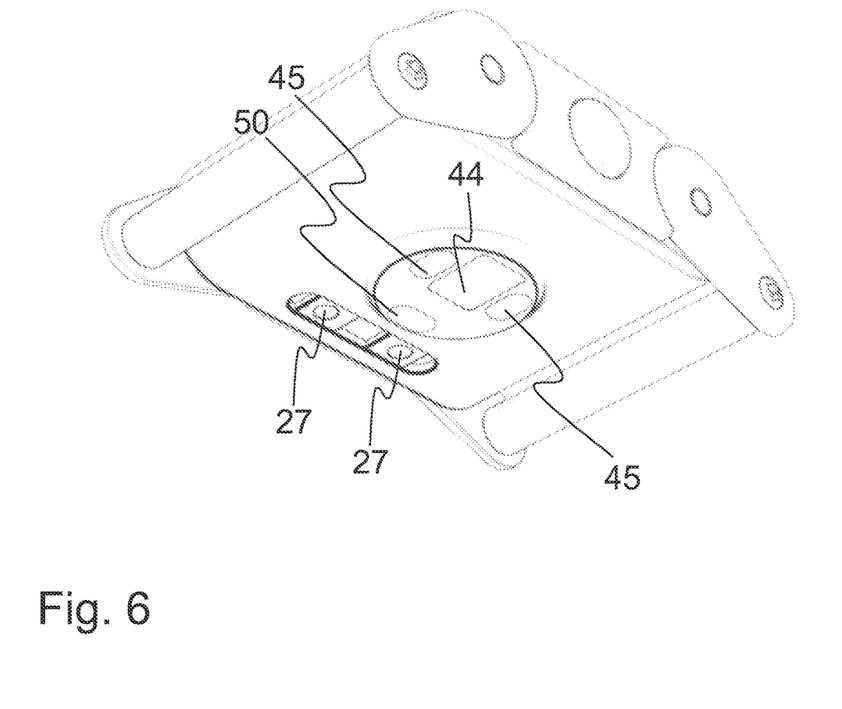
FIG. 6 shows a view of a biometric monitor from outside

An exploded view of an exemplary implementation of a biometric monitor is illustrated in FIG. 5. The optical sensor has two light detectors 40 and three green LEDs as light sources 41 arranged in line (not shown). In the figure the lenses 45 for the LEDs and the lenses 44 for the light detectors are shown. On one side of said line there is a further infra red LED having a lens 50. The charging clips 27 are shown on the bottom of the device. In the casing 20 there are corresponding apertures for said lenses and said charging clips A view of a biometric monitor from outside is shown in FIG. 6. A bump including the optical components can be seen in the middle of the bottom of the device. The lenses 44, 45, 50 of the optical components and the charging clips 27 are visible. In one example the apertures may contain adhesive instead of separate lenses 44, 45, 50.

Figure 7:
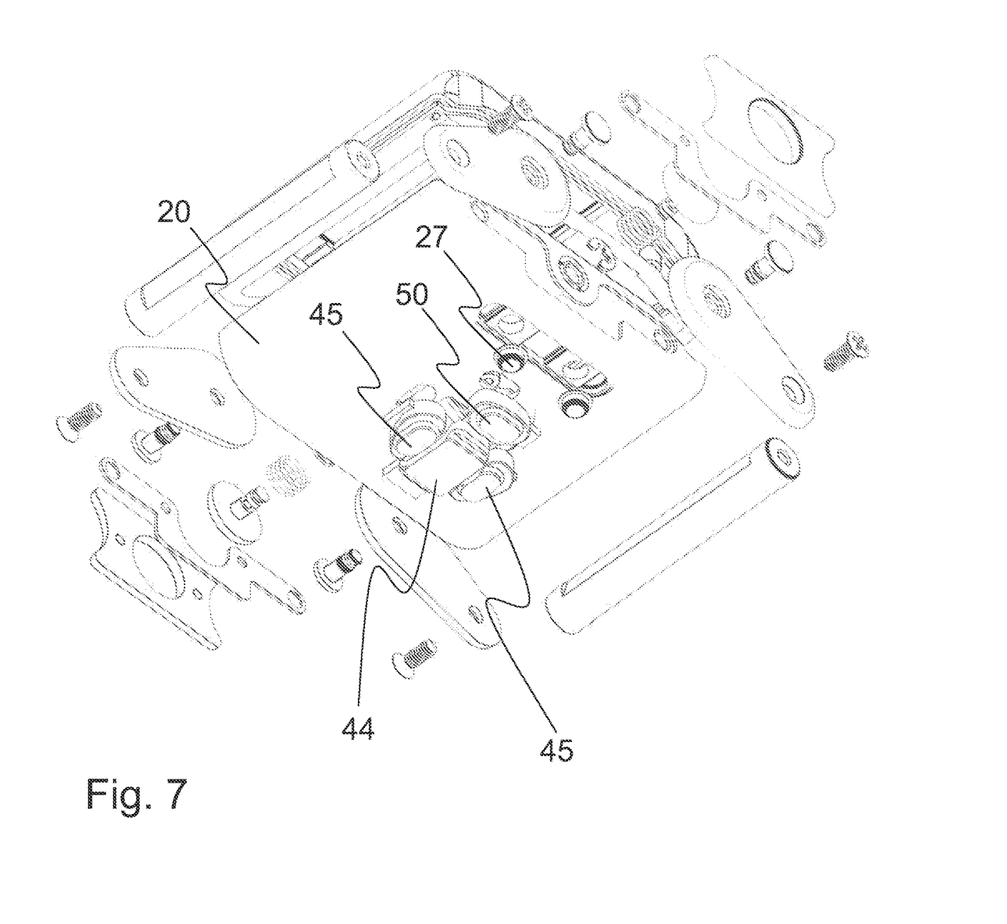
FIG. 7 shows an exploded view of a biometric monitor from outside

An exploded view of an exemplary implementation of a biometric monitor is illustrated in FIG. 7. The optical sensor has one light detector 40 and green LEDs as light sources 41 arranged in line (not shown). In the figure the lenses 45 for the LEDs and the lenses 44 for the light detectors are shown. On one side of said line there is a further infra red LED having a lens 50. The shape of the lenses can be seen. The lenses contain a narrower part which is configures to fit to the apertures in the casing, and a wider part which will be inside the casing.

The invention claimed is:

1. A portable biometric wrist device having an optical sensor and comprising
   a closed casing configured to be connectable to a wearable strap, wherein the closed casing encloses the entire portable biometric wrist device,
   at least one light source and at least one light detector installed inside the closed casing onto a circuit board inside the closed casing,
   the closed casing having at least one aperture for said at least one light source and at least one aperture for said at least one detector, and
   an opaque elastomer sealing plate arranged in contact with said closed casing and said circuit board, said sealing plate having an aperture surrounding and optically isolating each at least one light source and a separate aperture surrounding and optically isolating each at least one light detector.

2. The portable biometric wrist device of claim 1, comprising at least one lens inside the closed casing and optically connected with said at least one light source, and at least one other lens inside the closed casing and optically connected with said at least one light detector.

3. The portable biometric wrist device of claim 2, wherein the optical sensor contains adhesive between said at least one light source and said at least one lens optically connected to said light source, and/or between said at said at least one light detector and said at least one lens optically connected to said light detector.

4. The portable biometric wrist device of claim 2, wherein the optical sensor does not contain adhesive between said at least one light source and said at least one lens optically connected to said light source, and/or between said at said at least one light detector and said at least one lens optically connected to said light detector.

5. The portable biometric wrist device of claim 3, wherein the adhesive comprises epoxy adhesive.

6. The portable biometric wrist device of claim 3, wherein the light source has a cavity containing said adhesive.

7. The portable biometric wrist device of claim 1, wherein the optical sensor contains adhesive on said at least one light source and on said at least one light detector, said adhesive forming a transparent layer on said at least one light source and on said at least one light detector.

8. The portable biometric wrist device of claim 1, wherein the light source is a LED.

9. The portable biometric wrist device of claim 1, wherein the sealing plate comprises microcellular elastomer.

10. The portable biometric wrist device of claim 1, wherein the sealing plate comprises synthetic rubber, for example neoprene.

11. The portable biometric wrist device of claim 1, wherein the sealing plate comprises microcellular urethane.

12. The portable biometric wrist device of claim 1, wherein the optical sensor contains one light detector and two light sources within the closed casing.

13. The portable biometric wrist device of claim 1, wherein the sealing plate has a thickness in the range of 0.3-2.0 mm.

14. The portable biometric wrist device of claim 1, wherein the sealing plate has a thickness in the range of 0.3-1.0 mm.

15. The portable biometric wrist device of claim 1, wherein the sealing plate has a thickness in the range of 0.3-0.7 mm.

16. The portable biometric wrist device of claim 1, wherein the sealing plate contains adhesive on one or both sides.

17. The portable biometric wrist device of claim 1, wherein the closed casing is connected to a wearable wrist strap for attaching the portable biometric monitor to a user.

18. The portable biometric wrist device of claim 1, wherein the opaque elastomer sealing plate is arranged to fit as an intermediate layer between said closed casing and said circuit board.

19. A method for manufacturing a portable biometric wrist device having an optical sensor, the method comprising
   providing:
      a closed casing configured to be connectable to a wearable strap, wherein the closed casing encloses the entire portable biometric wrist device,
      at least one light source and at least one light detector installed onto a circuit board,
      the closed casing having at least one aperture for said at least one light source and at least one aperture for said at least one light detector, and
   arranging an opaque elastomer sealing plate arranged in contact with said closed casing and said circuit board, said sealing plate having an aperture for surrounding and optically isolating each at least one light source and a separate aperture for surrounding and optically isolating each at least one light detector,
   combining said circuit board and said sealing plate so that said at least one light source and said at least one light detector fit to the apertures in the sealing plate.

20. The method of claim 19, wherein the sealing plate comprises microcellular elastomer.

21. The method of claim 19, wherein the sealing plate comprises synthetic rubber, for example neoprene.

22. The method of claim 19, wherein the sealing plate comprises microcellular urethane.

23. The method of claim 19, wherein the sealing plate has a thickness in the range of 0.3-2.0 mm.

24. The method of claim 19, wherein the sealing plate has a thickness in the range of 0.3-1.0 mm.

25. The method of claim 19, wherein the sealing plate has a thickness in the range of 0.3-0.7 mm.

26. The method of claim 19, wherein the sealing plate contains adhesive on one or both sides.

27. The method of claim 26, comprising providing the sealing plate with adhesive on one or both sides with a release liner on the adhesive, and removing the release liner prior to arranging the sealing plate in contact with said closed casing and said circuit board.

28. The method of claim 27, comprising providing a stabilizing device, such as a jig, positioning the sealing plate onto the stabilizing device with the release liner still attached on the side which will be in contact with the stabilizing device, exposing the adhesive on the opposite side of the sealing plate, and positioning the part to be attached with the sealing plate onto the sealing plate on the stabilizing device in such way that the sealing plate will be attached onto said part.

29. The method of claim 19, comprising
applying adhesive onto said at least one light source and onto said at least one light detector.

30. The method of claim 29, comprising stabilizing said circuit board, said sealing plate and said at least one light source and said at least one light detector for the time the adhesives takes to cure.

31. The method of claim 29, comprising removing air bubbles from the adhesive before applying the adhesive, for example by using vacuum.

32. The method of claim 29, comprising providing at least one aperture in the circuit board for applying the adhesive, and injecting the adhesive from the opposite side of the circuit board through said at least one aperture onto said at least one light source and/or onto said at least one light detector, preferably after the circuit board and the sealing plate have been combined.

33. The method of claim 29, comprising connecting the closed casing to a wearable wrist strap for attaching the portable biometric monitor to a user.

34. The method of claim 19, comprising
further providing at least one lens for at least one light source and at least one lens for at least one light detector, and
placing said lenses to the apertures in the closed casing.

35. The method of claim 19, comprising arranging the opaque elastomer sealing plate to fit as an intermediate layer between said closed casing and said circuit board.

* * * * *